(12) United States Patent
Ausbourne et al.

(10) Patent No.: US 6,234,172 B1
(45) Date of Patent: May 22, 2001

(54) CONTROL AND DISPLAY CONFIGURATION LAYOUT

(75) Inventors: James Richard Ausbourne, Torrance; Robert Michael Garcia, Laguna Hills; Todd Douglas Kneale, La Habra; William Richard Sobko, Torrance; Louis Stephen Toth, La Palma; Peter A. Barnett, Costa Mesa; Douglas Ellwood Shultz, Brea, all of CA (US)

(73) Assignee: Integrated Medical Systems, Inc., Signal Hill, CA (US)

( * ) Notice: Subject to any disclaimer, the term of this patent is extended or adjusted under 35 U.S.C. 154(b) by 0 days.

(21) Appl. No.: 09/285,362

(22) Filed: Apr. 2, 1999

Related U.S. Application Data (63) Continuation-in-part of application No. 08/667,693, filed on Jun. 21, 1996, now Pat. No. 5,975,081.

(51) Int. Cl.$^7$ ................................................. A61G 15/00
(52) U.S. Cl. ........................................ 128/845; 128/897
(58) Field of Search ........................ 128/845, 846, 128/869, 870, 897; 5/621, 625, 626, 627, 628

(56) References Cited

U.S. PATENT DOCUMENTS

| | | |
|---|---|---|
| 117 | 7/1837 | Walford . |
| 1,200,852 | 10/1916 | Kern . |
| 1,258,694 | 3/1918 | Miller . |
| 1,287,855 | 12/1918 | Brand . |
| 2,704,989 | 3/1955 | Konecny ................ 114/0.5 |
| 2,837,778 | 6/1958 | Kern ........................ 20/2 |
| 3,050,331 | 8/1962 | Mansen .................... 296/27 |
| 3,148,911 | 9/1964 | Boyer et al. ............. 296/19 |
| 3,376,059 | 4/1968 | Corl ......................... 287/99 |
| 3,492,042 | 1/1970 | Nachtigall, Jr. ......... 296/24 |

(List continued on next page.)

FOREIGN PATENT DOCUMENTS

| | | |
|---|---|---|
| 9500477 | 2/1996 | (AU) . |
| 141669 | 12/1973 | (DE) . |
| 0343077 | 11/1989 | (EP) . |
| 1373384 | 11/1962 | (FR) . |
| 1473862 | 5/1977 | (GB) . |

OTHER PUBLICATIONS

Buchanan Aircraft Corporation Engineered Composites Spectrum Aeromed–Above and Beyond 1995.
MOBI—The Intensive Care Unit The Results of Innovative–Lifeport, Inc.
Mobile Intensive Care Rescue Facility (MIRF) Aeromed System, Inc.—Specification/AMT 300.

Primary Examiner—Michael A. Brown
(74) Attorney, Agent, or Firm—Stetina Brunda Garred & Brucker

(57) ABSTRACT

A transportable life support system for providing medical care to a patient while transporting the patient from one location to another has a platform configured to receive the patient, a plurality of medical devices attached to the platform for providing medical monitoring and medical therapy to the patient, and a control and display panel comprising controls and displays for the medical devices. The control and display panel provides a centralized location for monitoring and controlling the medical devices so as to mitigate a need for an operator to move about the platform in order to individually observe a display for each medical device and to individually control each medical device.

16 Claims, 5 Drawing Sheets

U.S. PATENT DOCUMENTS

| | | | |
|---|---|---|---|
| 3,531,151 | 9/1970 | Branfield | 296/23 |
| 3,761,968 | 10/1973 | Besler | 5/92 |
| 3,775,782 | 12/1973 | Rice et al. | 5/82 |
| 3,840,265 | 10/1974 | Stirling et al. | 296/19 |
| 4,060,079 | 11/1977 | Reinhold, Jr. | 128/145.8 |
| 4,161,172 | 7/1979 | Pickering | 128/1 |
| 4,224,936 | 9/1980 | Cox | 128/132 |
| 4,352,991 | 10/1982 | Kaufman | 307/9 |
| 4,425,978 | 1/1984 | Star | 180/243 |
| 4,680,790 | 7/1987 | Packard et al. | 379/432 |
| 4,715,385 | 12/1987 | Cudahy et al. | 128/710 |
| 4,724,844 | 2/1988 | Rafelson | 128/670 |
| 4,747,172 | 5/1988 | Hohol et al. | 5/507 |
| 4,757,811 | 7/1988 | Clark | 129/134 |
| 4,768,241 | 9/1988 | Beney | 5/60 |
| 4,780,919 | 11/1988 | Harrison | 5/60 |
| 4,783,109 | 11/1988 | Bucalo | 296/20 |
| 4,957,121 | 9/1990 | Icenogle et al | 128/897 |
| 4,981,139 | 1/1991 | Pfohl | 128/671 |
| 5,005,230 | 4/1991 | Congdon | 5/60 |
| 5,016,307 | 5/1991 | Rebar | 5/503 |
| 5,034,181 | 7/1991 | Billiu | 264/517 |
| 5,050,254 | 9/1991 | Murphy | 5/82 |
| 5,077,843 | 1/1992 | Dale et al. | 5/60 |
| 5,084,922 | 2/1992 | Louit | 5/81.1 |
| 5,092,722 | 3/1992 | Raezer, III et al. | 410/104 |
| 5,111,818 | 5/1992 | Suzuki et al. | 128/644 |
| 5,117,521 | 6/1992 | Foster et al. | 5/510 |
| 5,121,514 | 6/1992 | Rosane | 5/628 |
| 5,173,142 | 12/1992 | Billiu | 156/245 |
| 5,229,052 | 7/1993 | Billiu | 264/115 |
| 5,236,390 | 8/1993 | Young | 454/95 |
| 5,306,026 | 4/1994 | Jesse | 280/18 |
| 5,307,818 | 5/1994 | Segalowitz | 128/696 |
| 5,331,549 | 7/1994 | Crawford, Jr. | 364/413.02 |
| 5,335,651 | 8/1994 | Foster et al. | 128/202.13 |
| 5,338,588 | 8/1994 | Billiu | 428/36.3 |
| 5,342,121 | 8/1994 | Koria | 312/1 |
| 5,404,877 | 4/1995 | Nolan et al. | 128/671 |
| 5,421,340 | 6/1995 | Stanga et al. | 128/671 |
| 5,441,047 | 8/1995 | David et al. | 128/670 |
| 5,474,574 | 12/1995 | Payne et al. | 607/7 |
| 5,494,051 | 2/1996 | Schneider, Sr. | 128/870 |
| 5,497,766 | 3/1996 | Foster et al. | 128/200.24 |
| 5,511,553 | 4/1996 | Segalowitz | 128/696 |
| 5,570,483 | 11/1996 | Williamson | 5/83.1 |
| 5,590,648 | 1/1997 | Mitchell et al. | 128/630 |
| 5,615,430 | 4/1997 | Nambu et al. | 5/600 |
| 5,626,151 | 5/1997 | Linden | 128/897 |
| 5,630,238 | 5/1997 | Weismiller et al. | 5/600 |
| 5,664,270 | 9/1997 | Bell et al. | 5/600 |
| 5,680,661 | 10/1997 | Foster et al. | 5/618 |
| 5,687,717 | 11/1997 | Halpern et al. | 128/630 |
| 5,749,374 | 5/1998 | Schneider, Sr. | 128/870 |

CONTROL AND DISPLAY CONFIGURATION LAYOUT

RELATED APPLICATION

This patent application is a continuation-in-part patent application of U.S. Ser. No. 08/667,693, filed Jun. 21, 1996, now U.S. Pat. No. 5,975,081 and entitled SELF-CONTAINED TRANSPORTABLE LIFE SUPPORT SYSTEM, the contents of which are hereby incorporated by reference.

FIELD OF THE INVENTION

The present invention relates generally to medical devices which are utilized to treat intensive care patients and more particularly to a control and display subsystem for a self-contained transportable life support system such as those which are utilized in the resuscitation, stabilization, and transport of medical patients.

BACKGROUND OF THE INVENTION

It is frequently necessary to transport medical patients from the site of an accident or injury to a hospital. For example, persons suffering from casualties, trauma, or various medical emergency conditions such as heart attacks, and strokes must be transported quickly to a medical facility. Medical personnel speak of a "golden hour" within which such a medical patient must be transported to a medical facility so that proper medical care can be provided therefor. The survival rate for such medical patients is greatly enhanced if they are transported to the medical facility within that time.

As those skilled in the art will appreciate, it is frequently difficult to transport a patient to a remotely located medical facility in a timely manner, particularly within one hour. It is not unusual for accidents to occur at remote locations. Thus, a substantial amount of time may be required to transport the medical patient to a distant hospital. Also, in battlefield situations it is frequently impossible to transport a casualty immediately. In either instance, the patient may be located hundreds, if not thousands, of miles from the desired hospital, thus necessitating several hours of transport time. As such, it is frequently beneficial to perform various emergency medical procedures at the site of the medical problem, and then to attempt to provide ongoing medical care during transport to a remote hospital. The mortality rate of such transported medical patients is substantially reduced.

It is well-known to use various different medical devices in the field, i.e., at locations remote from a medical facility, so as to enhance a medical patient's chance of survival. For example, it is well-known to use an electrocardiograph (ECG) and a defibrillator upon heart attack victims so as to monitor the condition thereof and so as to provide medical treatment therefor in field.

Typically, the medical patient is placed upon a stretcher and then various different medical devices are used upon the patient, as necessary. During transport the medical devices may either be temporarily disconnected from the patient, or alternatively may be hand carried along therewith by additional personnel. However, disconnection of the medical devices from the patient results in the undesirable disruption of medical monitoring and/or treatment therefor. Hand carrying the medical devices along with the patient requires extra personnel, which may not be available, or for which there may not be adequate room within the transport vehicle.

As such, it is desirable to provide a system for transporting a medical patient wherein the medical devices are carried along with the stretcher. In an attempt to provide such a system for transporting a medical patient while facilitating the continuous use of medical devices thereupon, the Mobile Intensive Care Rescue Facility (MIRF) was developed by the Royal Australian Army Medical Corp. The MIRF is intended to provide sufficient medical equipment to have the capabilities of an intensive care hospital ward. The MIRF is designated so as to facilitate the removal and replacement of the various pieces of medical equipment therefrom for maintenance. The MIRF is specifically designed to accommodate two major roles: the transfer of critically ill people from one point to another, such as from a ward to an x-ray room or from one hospital to another; and the bringing of life support systems quickly to the scene of an accident or other medical emergency.

The MIRF can be configured to include a blood pressure cuff, an invasive blood pressure monitor, a body temperature sensor, a heart rate sensor (finger clip sensor), an oxygen saturation sensor, an exhaled air carbon dioxide sensor, and an electrocardiograph, so as to facilitate medical monitoring of a patient. Further, the MIRF can include a ventilation system, a volumetric infusion pump, a syringe pump, a suction unit, and a defibrillator so as to facilitate medical treatment.

Another contemporary system is the Mobile Intensive Care Unit (MOBI) described in United States Letters Patent No. 4,957,121, issued to Icenogle et al. on Sep. 18, 1990. The MOBI is similar to the MIRF in concept. That is, like the MIRF, the MOBI utilizes off-the-shelf medical devices which are attached to the housing thereof so as to be transportable therewith, thus eliminating disruptions in the medical care provided thereby during transport.

Further examples of such contemporary life support systems include those disclosed in U.S. Pat. Nos. 4,584,989; 4,352,991; 4,691,397; 3,304,116; and 3,341,246.

U.S. Pat. No. 4,584,989 discloses a life support stretcher bed adapted to accommodate patients in intensive or cardiac care units in hospitals. The life support stretcher bed is broadly adapted for electrical medical devices, medical supplies and features an undercarriage including a support structural, wheels, a patient housing with a mattress, an electrical power source and supports for mounting the medical equipment.

U.S. Pat. No. 4,352,991 teaches a life support system adapted for field use in a vehicle with available power and includes electrically operable life support units, means for supporting the life support units, a patient stretcher, and a DC power source adapted for battery or remote power source.

U.S. Pat. No. 4,691,397 teaches a device for carrying the life supporting devices of a bedridden patient including a table like means for supporting the devices, an IV holder, wheeled transport means and a hospital bed footboard securing means.

U.S. Pat. No. 3,341,246 teaches a hospital stretcher adapted broadly with a litter structure having telescopic post elements and other means for manipulating the patient to various positions.

As those skilled in the art will appreciate, it would further be desirable to monitor the operation of each of the medical devices so as to provide medical personnel with useful information regarding the patient's condition. Medical personnel could then use the results of such monitoring to determine the condition of the patient as well as the treatment which must be provided to the patient.

It is also desirable to locate the controls and indicators associated with each medical device at a common location.

Thus, there is no the need for an operator to move about the platform upon which the patient is disposed in order to individually observe a display for each medical device or to individually control each medical device. As such, it is desirable to provide means for monitoring and controlling each of the medical devices from a single location.

The ability to monitor all of the medical devices from a single location has the additional benefit of allowing the operator to observe changes in the display of one or more particular medical devices. The central location observations may substantially affect the patient's treatment by detecting events/conditions which may be missed if the operator is moving about the transportable life support system so as to observe each of the medical device's displays individually. For example, if the displays and indicators for the medical devices were not located together, then while the operator is observing one display, a change in another display may go unnoticed. If the change in the other display is transient in nature, then critical medical treatment may not be administered. Even if the change in the other display remains long enough for the operator to observe once the operator finally moves into a position to observe that display, then medical treatment has been delayed and may possibly be too late to provide the desired care.

It is further desirable to not only position the displays and indicators of the medical devices at a common location, but to do so in a manner which maintains integrity of prior governmental clearance of the medical devices. As those skilled in the art will appreciate, obtaining governmental clearance can be a time consuming and costly procedure. Thus, it would be preferable to utilize previously FDA cleared medical devices in a manner which does not invalidate their prior pedigree and clearance.

It is further desirable to position the controls and indicators of the medical devices in a manner which enhances thermal compatibility with the transportable life support system. More particularly, it is desirable to position the controls, data processors, and indicators such that cooling air passes thereabout before passing through the platform such that cooling of heat sensitive devices of the controls, processors, and displays is enhanced.

In a similar manner, it is desirable to position the controls, processors and displays in a manner which mitigates electromagnetic interference among components of the transportable life support system.

It is further desirable to attach the controls and indicators to the transportable life support system in a manner which facilitates easy removal and replacement thereof, and which substantially replicates the mounting provisions of the original equipment installations. It is also desirable to locate the controls and displays in a common location in an orientation relative to each other so as to optimize their access and functionality for particular medical procedures. The control and display subsystem of the present invention interfaces to the medical devices of the transportable life support system in a manner which does not substantially interfere with the operation thereof, thereby attempting to maintain integrity of the prior governmental premarket clearance, such as Food and Drug Administration (FDA) clearance of medical devices in the United States. This integrity is accomplished while repositioning the controls and displays of the individual medical devices subsystem at a common location, rather than having the controls and displays be co-located with the individual medical devices with which they are associated.

Thus, according to the present invention, the transportable life support system can assert adherence to predicate devices' features, safety, and efficacy within its governmental pre-market clearance process, since the individual medical monitoring devices and medical treatment devices thereof have already been cleared and since such prior governmental clearance integrity is asserted to be still valid after integration of the devices into the transportable life support system.

SUMMARY OF THE INVENTION

The present invention comprises a transportable life support system for providing medical care to a patient while transporting the patient from one location to another. The transportable life support system comprises a platform configured to receive the patient thereupon, a plurality of medical devices attached to the platform for providing medical monitoring and medical therapy to the patient, and a control and display head fairing comprising controls and displays for the medical devices. The control and display panel provides a centralized location for monitoring and controlling the medical devices so as to mitigate a need for an operator to move about the platform in order to observe a display for each medical device individually and to control each medical device individually However, although the medical devices are controlled from a centralized location, there is no common computer control of the medical devices. That is, none of the medical devices is controlled by a CPU which controls more than one medical device. The only CPU's used to control the medical devices are those which are integral components of the medical devices and which are substantially equivalent to those which were part of the medical devices as they were submitted for government clearance.

According to the preferred embodiment of the present invention, the control and display head fairing is disposed at the head end of the platform. Such positioning of the control and display interface allows the operator to be closer to the patient's head while monitoring and controlling the medical devices. Those skilled in the art will appreciate that such positioning of the operator is desirable because it provides the operator quicker access to the patient's chest and airway, which are likely to require medical attention in the event of an emergency and is the preferred location for patient physiological assessment and management during surgical procedures. During surgical procedures, devices on/under sides of the patient may be covered by sterile drapes or by attending medical personnel. The controls and displays of the medical devices preferably comprise the original controls and displays of the medical devices. That is, according to the preferred embodiment of the present invention, the medical devices are obtained having built in controls and displays. The built in controls and displays are then separated from the medical devices and repositioned in the control and display panel. The positioning of the controls and displays, as well as the electrical interconnection between the controls and displays and the medical devices, is accomplished in a manner which maintains integrity of prior government clearance of the medical devices. Thus, the electrical conductors between the medical devices and the controls and displays are merely lengthened so as to accommodate such repositioning of the medical displays and indicators, without introducing any circuitry which would tend to degrade the electrical signals transmitted therethrough. Further, no additional control circuitry is added. Only the original control circuitry is utilized.

Use of the original controls and displays for each medical device also mitigates the need for additional training, since many personnel will already be familiar with the original controls and displays.

The control and display head fairing is positioned upon the platform in a manner which enhances thermal compatibility therewith. More particularly, the control and display panel is positioned upon the platform such that cooling air passes around the control and display electrical components before passing through the platform, such that cooling of the heat sensitive devices of the control and display panel is enhanced. Those skilled in the art will appreciate that such cooling air tends to increase in temperature as it passes around electrical components. Therefore, allowing the cooling air to pass around the control and display components before passing through the platform provides cooler air to the heat sensitive devices of the control and display head faring. It will further be appreciated that many of the electrical components of the control and displays for the medical devices are temperature sensitive. In order to maintain reliable and efficient operation of the indicators and displays, it is desirable to regulate the temperature thereof.

The control and display panel is preferably removably attached to the platform in whole or in part, so as to facilitate easy removal and replacement of the controls and displays thereof.

The control and display panel is preferably positioned upon the platform in a manner which mitigates electromagnetic interference. As those skilled in the art will appreciate, electromagnetic interference between components of the transportable life support system is undesirable, since it may adversely affect the performance of the medical monitoring and medical therapy for the patient.

Positioning the controls and displays at a common location, i.e., the control and display head fairing, simplifies the procedures which may be practiced by an anesthesiologist, for example. Having the ventilator and other controls located proximate the patient's head minimizes the amount of movement that medical personnel, such as an anesthesiologist, must perform in order to properly care for the patient. All of the controls necessary for operating and monitoring the medical instruments are thus easily accessible. By way of contrast, in the MIRF, for example, such controls and displays with would be located beneath the patient, typically near the medical practitioners legs, where they are comparatively inaccessible.

Thus, according to the present invention, a method is provided for making a transportable life support system. The method comprises the steps of utilizing government cleared medical devices, re-locating controls and displays from the medical devices, and attaching the medical devices, which have had the controls and displays relocated and consolidated therefrom, to a platform which is configured to receive a patient thereupon. The medical devices are positioned relative to the platform in a manner which facilitates their use upon the patient. The controls and displays of the medical devices are attached to the platform at a common location to facilitate enhanced monitoring and control of the medical devices. The controls and displays of the medical devices are electrically connected to the medical devices in a manner which attempts to maintain integrity of prior governmental clearance of the medical devices. In the preferred embodiment nothing is added to the control circuitry which would substantially change the manner in which the medical devices are controlled.

DETAILED DESCRIPTION OF THE PREFERRED INVENTION

The detailed description set forth below in connection with the appended drawings is intended as a description of presently preferred embodiment of the invention, and is not intended to represent the only form in which the present invention may be constructed or utilized. The description sets forth the functions and the sequence of steps for constructing and operating the invention in connection with the illustrated embodiment. It is to be understood, however, that the same or equivalent functions may be accomplished by different embodiments that are also intended to be encompassed within the spirit and scope of the invention.

Figure 1:
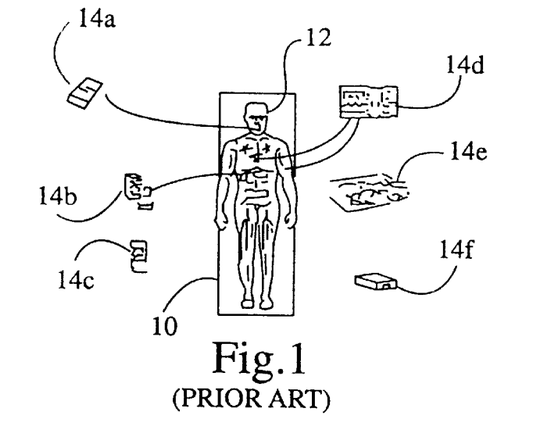
FIG. 1 shows a patient disposed upon a prior art transportable life support system 10, wherein a plurality of medical devices are being utilized to monitor the patient's condition and to provide medical treatment to the patient, the controls and displays of each of the medical devices being part of their associated medical devices, and thus being distributed around the patient according to the prior art.
Figure 2:
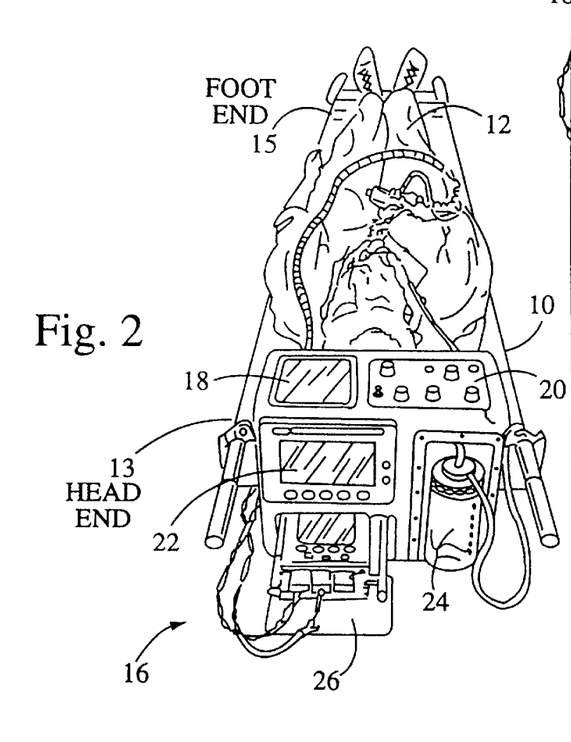
FIG. 2 is a perspective view of the head end of the transportable life support system, having controls and displays centrally located according to the present invention.
Figure 3:
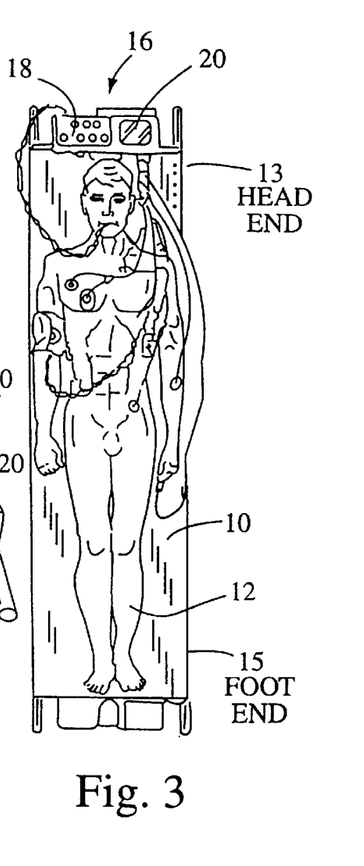
FIG. 3 is a top view of the transportable life support system of FIG. 2.
Figure 4:
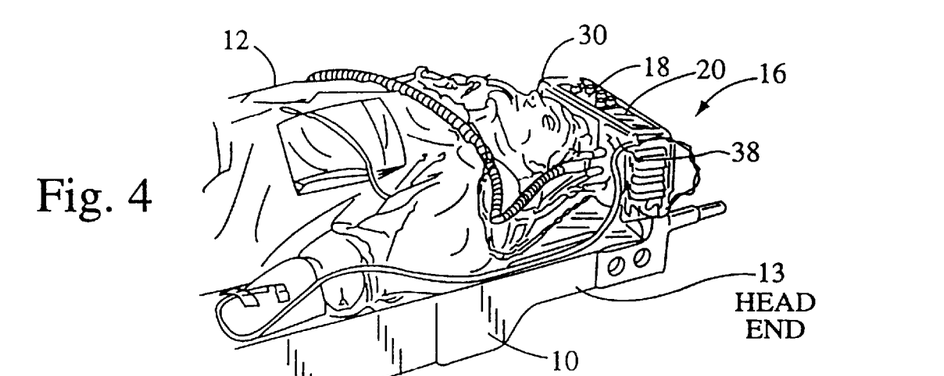
FIG. 4 is a perspective view of one side of the transportable life support system of FIG. 2.
Figure 5:
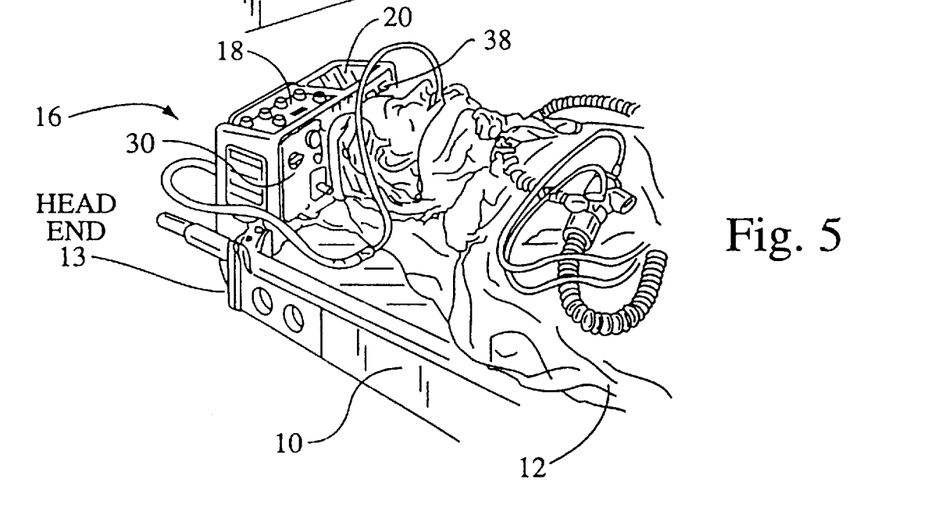
FIG. 5 is a perspective view of the other side of the transportable life support system of FIG. 2.
Figure 6:
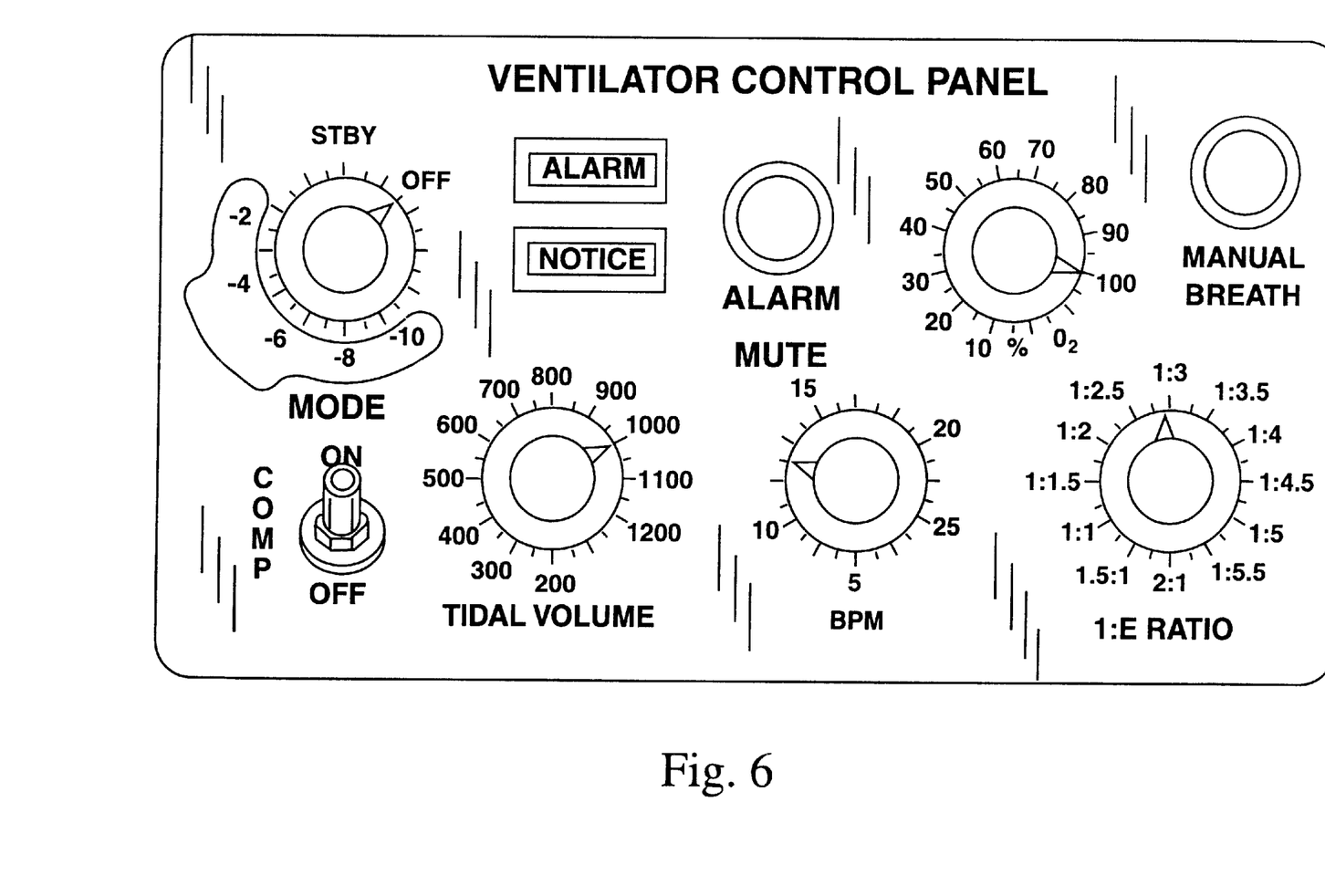
FIG. 6 is a front view of the ventilator control panel of the present invention.

The control and display subsystem for a transportable life support system of the present invention is illustrated in FIGS. 2–8 which depict a presently preferred embodiment thereof. FIG. 1 shows a prior art transportable life support system having the controls and displays of the various medical devices thereof co-located with the medical devices themselves.

Referring now to FIG. 1, according to the prior art a transportable life support system 10 having a patient 12 disposed thereupon has a plurality of life support devices 14a–14f disposed thereabout. The controls and displays associated with each of the medical devices 14a–14f are co-located with the medical devices 14a–14f themselves, such that an attendant or operator must move around the patient in order to monitor and effect control of each medical device. As described above, such moving around takes substantial time and causes the operator to focus his attention only upon the device being operated at the moment. More particularly, ventilator 14a, suction 14b, I.V./drug administration 14c, physiological monitors 14d, defibrillator 14e, and blood chemistry assessment 14f, are positioned at various different locations around the transportable life support system 10.

Thus, while the operator is monitoring and/or adjusting a particular medical device 14a–14f, another medical device 14a–14f, possibly located on the other side of the transportable life support system 10, may be providing a reading which would indicate the need for an adjustment thereof or some other medical attention for the patient 12. However, since the operator is disposed proximate the first medical device 14a–14f and is focusing his attention thereupon, the operator is not likely to see the displayed indication on the second medical device 14a–14f. Thus, the patient 12 may not receive optimum medical care.

As such, it would be beneficial to provide a centralized location for controls and displays of a plurality of different medical devices 14a–14f such that the operator can be located at a single position and from that position monitor and control each of the medical devices 14a–14f without moving about substantially. Thus, even though the operator may be focusing upon a particular medical device 14a–14f, any change in the display of another medical device 14a–14f is much more likely to catch the operator's attention, and therefor the operator is much more likely to provide the indicated medical treatment promptly. The original controls for each medical device are utilized, so there is no need to re-train personnel on how to operate the medical devices.

Referring now to FIGS. 2–5, a transportable life support system 10 has a control and display head fairing 16 disposed at the head end 13 thereof. As discussed in detail below, the displays and indicators from the various different medical devices 14a–14f of FIG. 1 are preferably located upon the control and display head fairing 16 such that the medical attendant or operator can position himself proximate the head end 13 of the transportable life support system 10, where critical medical procedures are commonly performed. From that position, an operator can monitor and control the operation of the various medical devices 14a–14f without moving about substantially. This consolidation of controls and displays not only reduces time and makes medical procedures much more efficient, but also allows the operator to observe indications from substantially all of the medical devices 14a–14f with comparatively little movement. As such, medical care is substantially enhanced, thereby possibly saving the patient's life or preventing debilitating aggravation of an injury. The remaining components or the medical devices themselves are located at various positions around the transportable life support system, as desired. That is, each of the medical monitoring and medical treatment components is positioned at a location where it can properly perform its intended function. Only the controls and displays thereof have been removed so as to facilitate their common location at the head end of the transportable life support system 10.

More particularly, the control and display head fairing 16 preferably comprises a liquid crystal display 18 or the like for displaying such parameters. The control and display head fairing 16 preferably further comprises a plurality of separately detachable portions, including ventilator control panel 20 (better shown in FIG. 6), a physiological monitor 22 for displaying ECG, pressure, temperature, $CO_2$ measurement, airway pressures, and tidal volume and the like on display 18, suction bottle 24 for showing the volume of fluid collected from the patient, infusion pump 26, suction control 30, oxygen status 34, ventilator connections 36, and defibrillator control and connections 38. The control and display head fairing 16 optionally further comprises system power control 32 and physiological monitor connectors 40.

Figure 7:
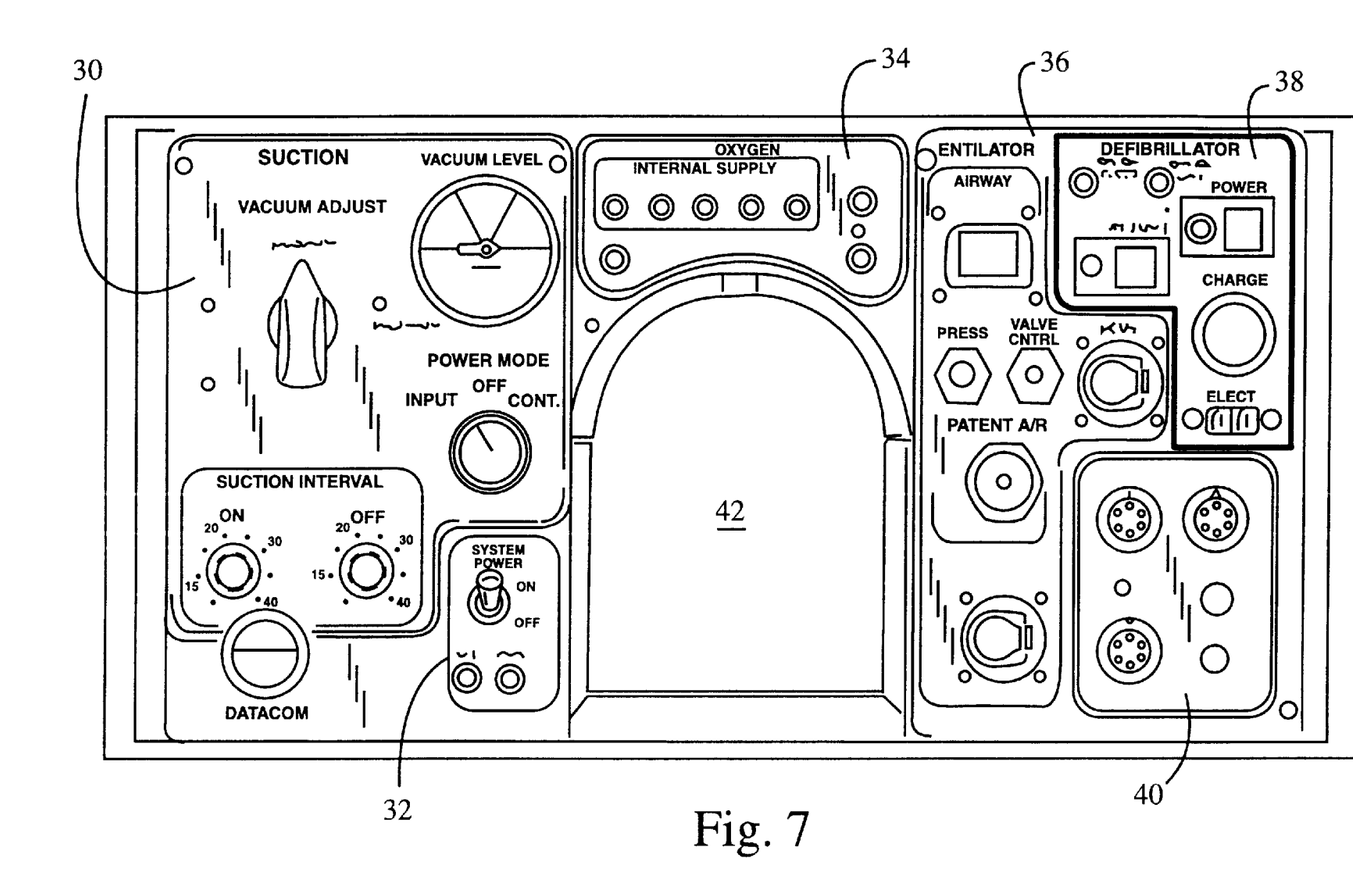
FIG. 7 is a front view of the operator/patient interface panel, including a suction control panel, oxygen status panel, ventilator interface panel, and defibrillator control panel of the present invention.

Referring now to FIG. 7, the suction control 30, power control 32, oxygen status 34, ventilator connections 36, defibrillator control 38, and physiological monitor connectors 40 are preferably arranged around a cushioned protrusion pad 42 formed to protect the head of the patient 12 from striking the panel/connectors.

Figure 8A:
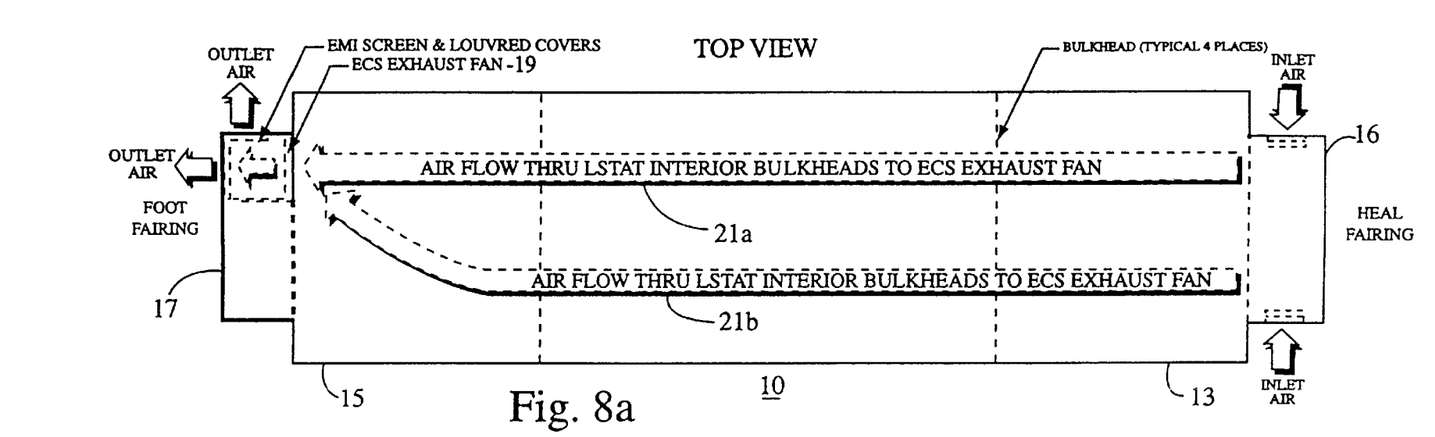
FIG. 8a is a top view of the transportable life support system, illustrating air flow therethrough.
Figure 8B:
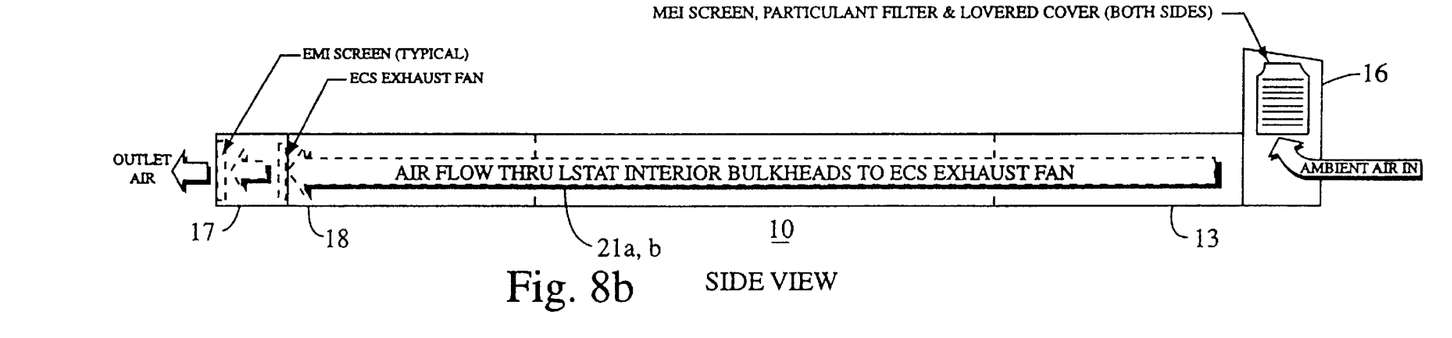
FIG. 8b is a side view of the transportable life support system, illustrating air flow therethrough.

Referring to FIG. 8a and 8b, the air flow through the transportable life support system is illustrated as shown therein. Air enters the transportable life support system 10 via inlet ducts formed in the head fairing 16. The air then passes adjacent electronic components in the head fairing, whereupon the air passes through one or more channels, such as 21a, 21b, towards foot fairing 17, disposed about foot end 15 of the transportable life support system 10. An exhaust fan 19, disposed in foot fairing 17, draws the air through channels 21a, 21b. The arrangement of the intake, outlet, in-patient orientation serve to achieve several functions simultaneously. The arrangement facilitates cooling the electronics and head fairing 16, while maintaining patient temperature and comfort levels. The location of the fan 19 remote from the electronics also serves to mitigate electromagnetic interference (EMI), attributable to fan operation. By locating the fan as remote as possible from the electronic devices, EMI is reduced.

Thus, the present invention provides a transportable life support system having controls and indicators of the medical devices thereof disposed at a common location in a manner which potentially does not invalidate the integrity of prior governmental clearance thereof. The structure and configuration layout facilitates cooling of the heat sensitive components thereof, and mitigates electromagnetic interference between components of the transportable life support system.

It is understood that the exemplary transportable life support system described herein as shown in the drawings represents only a presently preferred embodiment of the invention. Indeed, various modifications and additions may be made to such embodiment without departing from the spirit and scope of the invention. For example, the control and display panel may be located at another position, preferably proximate the head end of the transportable life support system, but alternatively at a side thereof or even at the foot end thereof. Further, those skilled in the art will appreciate that various different configurations or layouts for the various different controls and displays of the control and display panel are likewise contemplated. Thus, these and other modifications and additions may be obvious to those skilled in the art may be implemented to adapt the present invention for use in a variety of different applications.

What is claimed is:

1. A transportable life support system for providing medical care to a patient while transporting the patient from one location to another, the transportable life support system comprising:

a) a platform configured to receive the patient thereupon;

b) a plurality of medical devices attached to the platform for providing medical monitoring and medical therapy to the patient;

c) a control and display head fairing comprising controls and displays for the medical devices wherein the control and display head fairing provides a centralized location for monitoring and controlling the medical devices so as to mitigate a need for an operator to move about the platform in order to individually observe a display for each medical device and to individually control each medical device; and d) a ventilation system having at least one air intake duct disposed in the control and display head fairing, at least one air channel extending from the control and display head fairing to a foot end of the transportable life support system, and an exhaust fan disposed adjacent the foot end of the transportable life support system, the air flow path being arranged to cool controls and displays disposed in the head fairing, and maintain patient temperature control.

2. The transportable life support system as recited in claim 1, wherein the control and display head fairing is disposed at a head end of the platform.

3. The transportable life support system as recited in claim 1, wherein the controls and displays for the medical devices comprise original controls and displays of the medical devices.

4. The transportable life support system as recited in claim 1, wherein cooling air passes through the control and display head fairing before passing through the platform.

5. The transportable life support system as recited in claim 1, wherein the control, and display head fairing is configured to receive cooling air prior to the cooling air flowing into the platform, such that cooling of heat sensitive devices of the control and display components is enhanced.

6. The transportable life support system as recited in claim 1, wherein the control and display head fairing is formed of a plurality of separately detachable portions.

7. The transportable life support system as recited in claim 1, further comprising a shock isolation system for attaching the control and display head fairing to the platform in a manner which mitigates transmission of vibration/shock from the platform to the control and display head fairing.

8. The transportable life support system as recited in claim 1, wherein the control and display panel is positioned upon the platform remote from the exhaust fan to mitigate electromagnetic interference in the operation of controls and devices disposed in the head fairing.

9. A transportable life support system for providing medical care to a patient while transporting the patient from one location to another, the transportable life support system comprising:

a) a platform configured to receive the patient thereupon;

b) a plurality of medical devices attached to the platform for providing medical monitoring and medical therapy to the patient;

c) a control and display head fairing comprising controls and displays for the medical devices wherein the control and display head fairing provides a centralized location for monitoring and controlling the medical devices so as to mitigate a need for an operator to move about the platform in order to individually observe a display for each medical device and to individually control each medical device; and d) a shock isolation system for attaching the control and display head fairing to the platform in a manner which mitigates transmission of vibration/shock from the platform to the control and display head fairing.

10. The transportable life support system as recited in claim 9, wherein the control and display head fairing is disposed at a head end of the platform.

11. The transportable life support system as recited in claim 9, wherein the controls and displays for the medical devices comprise original controls and displays of the medical devices.

12. The transportable life support system as recited in claim 9, further comprising a ventilation system having at least one air intake duct disposed in the control and display head fairing, at least one air channel extending from the control and display head fairing to a foot end of the transportable life support system, and an exhaust fan disposed adjacent the foot end of the transportable life support system, the air flow path being arranged to cool controls and displays disposed in the head fairing, and maintain patient temperature control.

13. The transportable life support system as recited in claim 12, wherein cooling air passes through the control and display head fairing before passing through the platform.

14. The transportable life support system as recited in claim 12, wherein the control and display panel is positioned upon the platform remote from the exhaust fan to mitigate electromagnetic interference in the operation of controls and devices disposed in the head fairing.

15. The transportable life support system as recited in claim 9, wherein the control, and display head fairing is configured to receive cooling air prior to the cooling air flowing into the platform, such that cooling of heat sensitive devices of the control and display components is enhanced.

16. The transportable life support system as recited in claim 9, wherein the control and display head fairing is formed of a plurality of separately detachable portions.

* * * * *